(12) United States Patent
Khanuja et al.

(10) Patent No.: US 7,375,260 B2
(45) Date of Patent: May 20, 2008

(54) HIGH ARTEMISININ YIELDING ARTEMISIA PLANT NAMED 'CIM-AROGYA'

(75) Inventors: Suman Preet Singh Khanuja, Uttar Pradesh (IN); Shilpi Paul, Uttar Pradesh (IN); Ajit Kumar Shasany, Uttar Pradesh (IN); Anil Kumar Gupta, Uttar Pradesh (IN); Mahendra Pandurang Darokar, Uttar Pradesh (IN); Madan Mohan Gupta, Uttar Pradesh (IN); Ram Kishor Verma, Uttar Pradesh (IN); Govind Ram, Uttar Pradesh (IN); Anuraddha Kumar, Uttar Pradesh (IN); Raj Kishori Lal, Uttar Pradesh (IN); Ravi Prakash Bansal, Uttar Pradesh (IN); Anil Kumar Singh, Uttar Pradesh (IN); Rajendra Singh Bhakuni, Uttar Pradesh (IN); Sudeep Tandon, Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 159 days.

(21) Appl. No.: 11/334,333

(22) Filed: Jan. 18, 2006

(65) Prior Publication Data

US 2007/0089211 P1    Apr. 19, 2007

Related U.S. Application Data

(63) Continuation of application No. 10/811,244, filed on Mar. 26, 2004, now abandoned.

(51) Int. Cl.
*A01H 5/00* (2006.01)
(52) U.S. Cl. ..................................................... 800/298
(58) Field of Classification Search ................. 800/298
See application file for complete search history.

(56) References Cited

U.S. PATENT DOCUMENTS

| 6,127,405 | A | 10/2000 | Kumar et al. |
|---|---|---|---|
| 6,393,763 | B1 | 5/2002 | Kumar et al. |
| PP12,788 | P2 * | 7/2002 | Harnett |
| 6,423,741 | B1 | 7/2002 | Khanuja et al. |
| PP16,046 | P3 * | 10/2005 | Speichert |
| 2005/0223447 | P1 * | 10/2005 | Khanuja et al. |
| 2007/0089211 | P1 * | 4/2007 | Khanuja et al. |

\* cited by examiner

*Primary Examiner*—Wendy C. Haas
(74) *Attorney, Agent, or Firm*—Ladas and Parry LLP

(57) ABSTRACT

The present invention is related to the development of a novel, distinct high herb and artemisinin yielding genotype of *Artemisia annua* obtained through systematic marker assisted breeding followed by selection of uniform population in a methodical way wherein the genotype is distinct, uniform and stably maintainable by continuous rouging of off types in the population using DNA marker at early seedling stage from nursery itself and suitable for commercial cultivation.

1 Claim, 1 Drawing Sheet

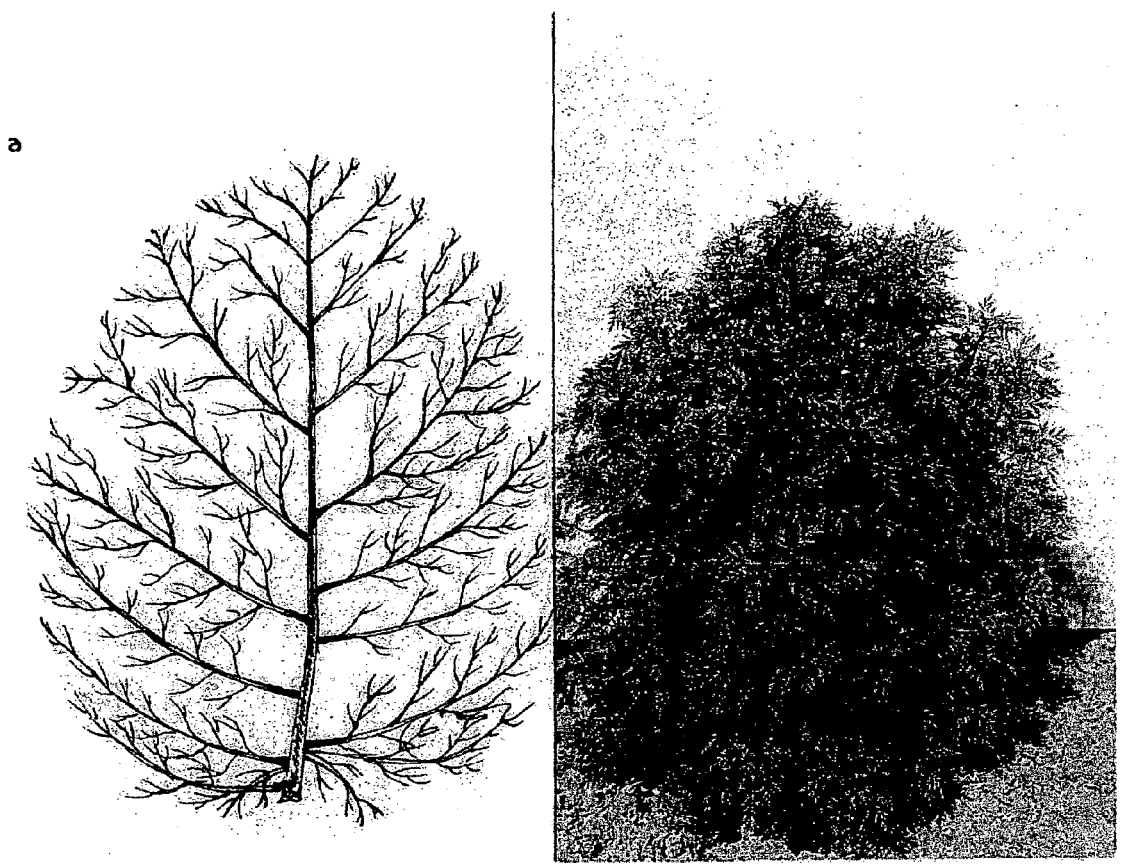
FIG.1 The plant along with the architecture

HIGH ARTEMISININ YIELDING ARTEMISIA PLANT NAMED 'CIM-AROGYA'

This application is a continuation of application Ser. No. 10/811,244 filed on Mar. 26, 2004, now abandoned claims the benefit thereof and incorporates the same by reference.

FIELD OF THE PRESENT INVENTION

The present invention was related to the development of a novel, distinct high herb and artemisinin yielding genotype of *Artemisia annua* obtained through systematic marker assisted breeding followed by selection of uniform population in a methodical way. This invention further relates to marker assisted breeding to reach the high artemisinin yielding genotype. The genotype is distinct, uniform and stably maintainable by continuous rouging of off types in the population using DNA marker at early seedling stage from nursery itself and suitable for commercial cultivation.

BACKGROUND AND PRIOR ART REFERENCES OF THE PRESENT INVENTION

Many *Artemisia* species are cited by early herbalists including Theophrastus in the third century B.C (Einarson and Link, 1976), Pliny (Bostock and Riley, 1855-1857) and Dioscorides (Gunther, 1959) in the first century BC. Wormwood (probably the species *A. judaica*) is mentioned in the Bible (Rev 8:10, 11). In 340 AD, Ge Hong prescribed aerial part of *Artemisia* for the treatment of fever in the "Chinese hand book of prescriptions for emergency treatments" and in 1527, Li Shi Zhen, a Chinese herbalist/pharmacologists mentioned the use of *huang hua hao* (or yellow flower, later identified as *A. annua*) for treatment of children's fever and qinghao (*A. apiacea*) as a treatment for the disease now known as malaria.

The plant *Artemisia annua* (family: Asteraceae) produces a sesquiterpenoid lactone endoperoxide named artemisinin which is a promising antimalarial drug effective against *Plasmodium falciparum, Plasmodium vivax* at nanomolar concentration. Artemisinins are active against *Schistosoma mansoni* and *S. japonicum* in-vitro and in-vivo in experiments in animals. These schistosomes, like malarial parasites, degrade haemoglobin and produce hemozoin. These compounds are also active against *Leishmania major, Toxoplasma gondii* and *Pnenmocystic carinii* in-vitro and against *P. carinii* in-vivo. Artemisinins have immunosuppressive activity and also potential anticancer activity. For these activities, the doses of artemisinin required are substantially higher than the dose for antimalarial activities. According to Meshnick et at., (1996) (Microbiological Reviews 6:301-315) the antimalarial endoperoxides including artemisinin, dihydroartemisinin and arteethers, are not likely to be useful for other therapeutic purposes except against malarial parasites.

Although artemisinin rapidly suppresses the activity of parasites like *Plasmodium vivax* and *P. falciparum*, problems with high rate of recrudescence (>10% recrudescence infections), short half life persist. Hence, there is a need to develop new drugs against quinolone resistant pathogenic bacteria. It is a known fact that clinically used antibacterial broad spectrum compounds such as quinolones which exhibit DNA gyrase activity of *Mycobacterium* sp. (causing tuberculosis), *Haemophilus* sp. and *Haemophilus influenzae* are gradually becoming ineffective due to the occurrence of mutatious in gyrase genes and their natural selection under continuous use of such drug. The compound α arteether developed as antimalarial drugs by Central Drug Research Institute (CDRI), Lucknow, India and Central Institute of Medicinal & Aromatic Plants (CIMAP), Lucknow, India, after phase II clinical trial is a stable derivative of artemisinin. Earlier we have found a novel property of α-arteether as being effective against the gyr A mutant strains of *E. coli* but ineffective against wild type strains (U.S. Pat. No. 6,127,405). Also we have developed a strategic and novel composition comprising α arteether and nalidixic acid or quinolone drugs which is useful as an advanced generation drug to counter the resistance development itself and having a potential to be used in treating infectious diseases and in inhibiting the resistance developed due to mutation in the gyr A gene of bacteria, particularly in those cases where drug resistant strains are known to appear very frequently (U.S. Pat. No. 6,423,741). We have already reported a genotype 'Jeevanraksha' earlier yielding more than 1% artemisinin (Sushil Kumar, S Banerjee, S Dwivedi, M M Gupta, R K Verma, D C Jain, S P S Khanuja, A K Mathur, G D Bagchi, M Zehra, V K Mehta, A A Naqvi, S Paul, G Ram, M Ram, D Saikia, R S Sangwan, T R Santha Kumar, A K Shasany, M P Darokar, A K Singh, A Singh (1999) Registration of Jeevanraksha and Suraksha varieties of the antimalarial medicinal plant *Artemisia annua*. Jour. Med. Arom. Plant Sci. 21: 47-48.) and the method to increase yield through harvesting management (U.S. Pat. No. 6,393,763).

It is always beneficial to have diversity in genotypes in different background than a single genotype for commercial cultivation. With this objective a novel genotype was developed through a novel method of DNA marker assisted breeding.

OBJECTS OF THE PRESENT INVENTION

The main object of the present invention is to develop a novel, distinct high herb and artemisinin yielding genotype of *Artemisia annua*.

SUMMARY OF THE PRESENT INVENTION

The present invention was related to the development of a novel, distinct high herb and artemisinin yielding genotype of *Artemisia annua* obtained through systematic marker assisted breeding followed by selection of uniform population in a methodical way. This invention further relates to marker assisted breeding to reach the high artemisinin yielding genotype. The genotype is distinct, uniform and stably maintainable by continuous rouging of off types in the population using DNA marker at early seedling stage from nursery itself and suitable for commercial cultivation.

DETAILED DESCRIPTION OF THE PRESENT INVENTION

Accordingly, the present invention relates to a new and distinct genotype of *Artemisia annua* 'CIM-Arogya', developed through marker assisted breeding, possessing the following combination of characters:

Genus: *Artemisia*
Species: *annua*
Family: Asteraecae
Common name: Qinghao
Plant height: 280-305 cm
Plant canopy: Oval
Growth habit: Erect
Branching: sympodial branching pattern Stem: Single, round hard woody green (137D) Stem width 5-12 cm (app)
Number of branches:—
Primary branches.—55-65
Secondary branches per primary branch:—50-60—
Tertiary branches per secondary branch:—37-45
Range of length of internodes
Main stem—4-6 cm at bottom, 10-12 cm at middle, 2-5 cm at the top
Primary branch—2-5 cm at bottom, 8-11 cm at middle, 2-4 cm at the top
Secondary branch—8-11 cm at the bottom, 5-7 cm at the middle, 1-3 cm at the top
Tertiary branch—3-5 cm at the bottom, 1-3 cm at the middle, 0.5-1.5 cm at the top
Leaf—Green (137 B)
Texture—Thin and flexible
Surface—Smooth non pubescent
Shape—Pinnately compound leaf
Margin—Pinnetisected
Tip—Acute
Petiol length—2.5-3.50 cm
Lamina length—5-7 cm
Lamina width—4-5 cm
Inflorescence—Capitulum (head)
Flower—rranged in whorls. Colour yellow group (7A)
Two types of flowers—Disc florets and Ray florets.
Disc florets are bisexual and ray florets are unisexual (female)
Colour—Greenish yellow 2-3mm in diameter
Receptacles—Glabrous
Calyx—Bracteates
Corolla—Sympelatous, tubular top split in to 5 lobes in Disc florets and 2-3 lobes in Ray florets (legulate)
Androecium 5 stamens, Anther lobes are fused and filaments are free
Colour—Yellowish
Gynoecium Unilocular, inferior bifid stigma.
Colour—yellowish
Time of flowering—198 days.
Seed setting 240 days (app)
Artemisinin content 0.9 to 1.1%
Artemesinic acid: 0.002-0.004%
Oil content: 0.35-0.45%
alternate deeply dissected aromatic leaves ranging between 25 to 50 cm in length.
tiny yellow nodding flowers (capitula)
capitula in loose panicle containing numerous central bisexual florets and marginal pistillate florets
receptacle is glabrous
florets and receptacle bear abundant 10-celled biseriate trichomes
globular canopy
dry leaf yield of about 50 Q per hectare
flowers (7A) arranged in a head or Capitulum,

BRIEF DESCRIPTION OF THE ACCOMPANYING DRAWINGS

FIG. 1 shows the plant along with its architecture "CIM-Arogya"

The research on genome analysis is being taken up as a necessity to understand the genomic constitution of individuals in terms of DNA content, nature and variations etc. The data from gnome analysis are of direct relevance to molecular plant breeding in which morphological characters can be tagged to unique DNA sequences and then inheritance patterns of DNA markers can be utilized to confirm the presence of traits even before expression. Techniques are available to differentiate even similar looking individuals of a population on the basis of DNA sequence variation. Some recent important discoveries from application point of view towards genetic analysis include Restriction endonucleases mapping and Polymerised Chain Reaction for amplifying DNA sequences from traces. These discoveries have led to the means and techniques used to study the differences or uniqueness in the DNA sequences otherwise known as Polymorphism in the DNA. The tools like RAPD, AFLP, RFLP, micro-satellite and many others were invented earlier and used in literature extensively for differentiating and marking the plants for different characters.

Development of Marker Correlating to High Content of Artemisinin in the Plant *Artemisia annua*.

Selection of Genotypes

The seeds of ten chemotypic accessions of the plant *Artemisia annua* were selected from Kashmir and further studies were carried out in Lucknow field station. Seeds of *A. annua* were sown in pots with mixture of soil and FYM (farmyard manure) in the ratio of 1:1 and germination in glass house conditions during the month of November of the years 1998-2001. The seedlings having 10 cm height were transplanted with spacing 50 cm between rows and 30 cm between plants. The soil of experimental field was sandy loam in texture and neutral in reaction (pH 7.6). The plots were fertilized with FYM (Farm yard manure) @20 kg\ha before transplanting for obtaining optimum performance. Plots were prepared 3 m×3 m size with irrigation channels. For Hybridization, six seed lots were selected out of 10 seedlots (obtained from Kashmir in the year 1998) were transplanted in alternative rows. From the next year (1999) on wards the progeny seedlings of the chemotypically selected plants were planted again in alternate rows. All the seedlings were checked for artemisinin content after extraction. About 0.1 g dry powdered plant material was extracted in 10 ml of hexane by heating at 60° C. for 3 minutes and left for overnight at room temperature. Then extract was filtered and evaporated on water bath at 50° C. After evaporation extract was dissolved in 1 ml hexane and used in TLC. Properly (20×20 cm E-MEREK) dissolved extract was spotted in TLC plates at 1 cm apart along with standard (1 mg\ml). Spotted TLC plate was dipped in solvent (mobile phase) Hexane:Diethyl ether (1:1) Plate was dried in air and dipped in developing reagent Glacial acetic acid:conc. Sulphuric acid:Anisaldehyde (50:1:0.5 ml) and heated at 120° C. for 10-15 minutes and then Stabilized and scanned (540 nm, visible) (Densitometer CAMAG: Switzerland). The TLC plates were scanned and the artemisinin content of individual progeny plants were quantified. From the analysis the plants producing trace (0.10% or less) artemisinin and the plants producing more than 0.4% artemisinin were selected and finally 10 plants from each category were taken for DNA analysis.

DNA Isolation and PCR Amplifications

DNA was isolated from the leaf tissue essentially according to the protocol described earlier (Khanuja S P S, Shasany A K, Darokar M P, Sushil Kumar (1999) Rapid Isolation of PCR Amplifiable DNA from the Dry and Fresh Samples of Plants Producing Large Amounts of Secondary Metabolites and Essential oils by Modified CTAB Procedure. *Plant Molecular Biology Reporter*, 17, 74.). Polymerase chain reactions (PCRs) were carried out in 25 µl volume. A reaction tube contained 25 ng of DNA, 0.2 unit of Taq DNA polymerase, 100 μM of each dNTPs, 1.5 mM MgCl$_2$ and 5 pmol of decanucleotide primers. The amplifications were carried out using the DNA Engine thermal cycler (MJ Research, USA) using 94° C., 35° C. and 72° C. temperatures for 40 cycles (Khanuja S P S, Shasany A K, Srivastava A, Sushil Kumar (2000). Assessment of genetic relationships in *Mentha* species. *Euphytica*, 111, 121-125.). The amplified products were separated on 1.2% agarose gel containing 0.5 μg ml$^{-1}$ of ethidium bromide and photographed with Image master VDS (Pharmacia). The bands were analyzed using Image master 1D elite software and the graphic phenogram of the genetic relatedness among the accessions was produced by means of UPGMA (unweighted pair group method with arithmetic average) cluster analysis. Custom-made decanucleotide primers were synthesised in the laboratory on Applied Biosystems 392 DNA-RNA Synthesizer and were designated as MAP01 to MAP20.

The sequences of the primers MAP01 to MAP20 were AAATCGGAGC, GTCCTACTCG, GTCCTTAGCG, TGCGCGATCG, AACGTACGCG, GCACGCCGGA, CACCCTGCGC, CTATCGCCGC, CGGGATCCGC, GCGAATTCCG, CCCTGCAGGC, CCAAGCTTGC, GTGCAATGAG, AGGATACGTG, AAGATAGCGG, GGATCTGAAC, TTGTCTCAGG, CATCCCGAAC, GGACTCCACG, AGCCTGACGC, respectively. The other sets of primers used included kit J, O and T, each consisting of 20 random decamer primers, procured from Operon Technologies Inc., USA.

All the RAPD profiles thus generated were analyzed for bands always appearing with all the high artemisinin containing genotypes (more than 0.4%) and absent in the genotypes containing trace or no artemisinin. We could detect a band at approximately 850 base pair region amplified with the primer 5'CCAAGCTTGC3' (MAP 12, Sequence ID 1) which consistently showed its presence in the genotypes containing more than 0.4% artemisinin and absent in the genotypes with trace or no artemisinin. This finding was interesting considering the complex nature of the artemisinin biosynthetic pathway. For all other primers the amplified products showed variable positions in these genotypes and could not be correlated. The presence of the band in the segregating populations having high artemisinin could be ascertained as the samples of 10 analyzed plants having high artemisinin were drawn from different populations. Similarly, the sample of 10 plants for trace or no artemisinin drawn from different populations could show always the absence of the band. As all the plants analyzed were from the same initial population the genes for artemisinin biosynthesis were assumed to be normal. So the presence and absence of the band could be correlated to the regulatory function associated with the expression of some of the genes associated with the biosynthetic pathway. But certainly the DNA band of about 850 base pair size could be correlated with the biosynthesis of more than 0.4% artemisinin in *Artemisia annua*.

In the next steps the DNA fragment described earlier was eluted out from the agarose gel and (since the fragment was amplified with the primer containing Hind III restriction site) restricted with Hind III restriction enzyme (Recognition and restriction site 5'AAGCTT3'). Similarly, pBluescript II SK(+) procured from Stratagene Inc. was used to clone the fragment at the Hind III site using T4 DNA ligase enzyme available commercially. *Escherichia coli* strain DH5α, procured from Stratagene Inc again was transformed with this constructed plasmid and transformed cells were isolated on agar plates containing nutrient broth and ampicillin. All the experiments were performed according to the protocol Sambrook et al (1988).

This fragment was sequenced completely with the help of M13 forward and T3 reverse primer (the sequence sites are present in the plasmid pBluescript II SK(+) and the nucleotide sequence is given below.

```
  1 AAGCTTGCTG AACGCATCGG TGTTACTGCC GCAGCCCGTG
    AACTCAGCCT GTATGAATCA

61 CAACTCTACA ACTGGCGCAG TAAACAGCAA AATCAGCAGA
    CGTCTTCTGA ACGTGAACTG

121 GAGATGTCTA CCGAGATTGC ACGTCTCAAA CGCCAGCTGG
    CAGAACGGGA TGAAGAGCTG

181 GCTATCCTCC AAAAGGCCGC GACATACTTC GCGAAGCGCC
    TGAAATGAAG TATGTCTTTA

241 TTGAAAAACA TCAGGCTGAG TTCAGCATCA AAGCAATGTG
    CCGCGTGCTC CGGGTGGCCC

301 GCAGCGGCTG GTATACGTGG GTGTCAGCGG CGGACAAGGA
    TAAGCCCGCG TAAGCAGTTC

361 CGCCAACACT GCACAGGG GG TTGTCTCGCG GGTTTTACCC
    CGGGTCAAAC AAGCGTTACC

421 GGTGCCCCAC GCTTGACCGG ATGACCTGCG GTGCTCAGGG
    TTACCCTTTA ACGTAAAAAA

481 CCCGTGGCGG CAAGCTTGCC CGGTCAGGGA CTGAAGGCAA
    AGGCCTCCCG GAAGTTCAGC

541 CCGGTCAGCT ACCGCGGCAC ACGGGCCTGC CTGTGTCAGA
    AAATCTGTTG GAGCAGGATT

601 TTTACGCCCA GTGGCCCGAA CCAGAAGTGG GCAGGAGACA
    TCACGTACTT ACGTACAGAT

661 GAAGGCTGGC TGTATCTGGC AGTGGTCATT GACCTGTGGT
    CACGTGCCGT TATTGGCTGG

721 TCAATGTCGC CACGCATGAC GGCGCAACTG GCCTGCGATG
    CCCTGCAGAT GGCGCTGTGG

781 CGGCGTAAGA GGCCCCGGAA CGTTATCGTT CACACGGACC
    GTGGAGGCCA GTACTGTTCA

841 GCAGATTATC AGGCGCAACT GAAGCGGCAT AATCTGCGTG
    GAAGTATGAG CGCAAAAGGT

901 TGCTGCTACG ATAATGCCTG CGTGGAAAGC TT
```

Based on the sequence at the ends forward and reverse primers were synthesized with the sequence

```
Forward Primer   5'CCAAGCTTGCTGAACGCATCGG3'

Reverse primer   5'CCAAGCTTGCCACGCAGGCATTATC3'
```

These sequences were used to amplify the genomic DNA of *Artemisia annua* (both high content of artemisinin and low content of artemisinin). The plant genomic DNA with high artemisinin content could generate a band of 936 bp where as in plants containing low amount of artemisinin the absence of the band was conspicuous.

Use of the Marker to Generate a Population of Plants with High Artemisinin Content.

In the first year polycross nursery was designed with alternate male and female line chosen among the seedlots. These plants were randomly picked up from the nursery raised from the 6 selected seed lots. The plants, which were designated as female (270 plants), were analyzed for artemisinin content, which were selected for further experimentation. Seed sample were collected from these selected plants (13 in number) containing high amount of artemisinin (0.15 to 0.20%) and planted again in a polycross nursery in the second year. Next year 180 plants were analyzed for artemisinin content and 13 plants containing 0.45 to 0.50% artemisinin were selected for planting in the third year. At this point 10 plants With more than 0.4% artemisinin and 10 plants containing trace amount artemisinin were taken for DNA isolation to develop SCAR marker as described previously. The SCAR marker was used to select plants from the nursery raised from the seeds selected 13 seedlots, and 12 plants from each seedlots showing the presence of SCAR marker were selected for random crossing among the plants in the third year. Randomly plants were analyzed for artemisinin content and among 150 plants analyzed 20 plants having artemisinin 0.8 to 1.0% were selected for next year (fourth year) planting. The seeds from these plants were grown in the nursery and 12 SCAR positive plants from each seed lot were grown randomly to facilitate cross pollination. From these 200 plants were analysed for artemisinin content and 11 plants were selected having 1.0 to 1.16% artemisinin content. Simultaneously, increase in the mean artemisinin content of the plants analysed every year were calculated.

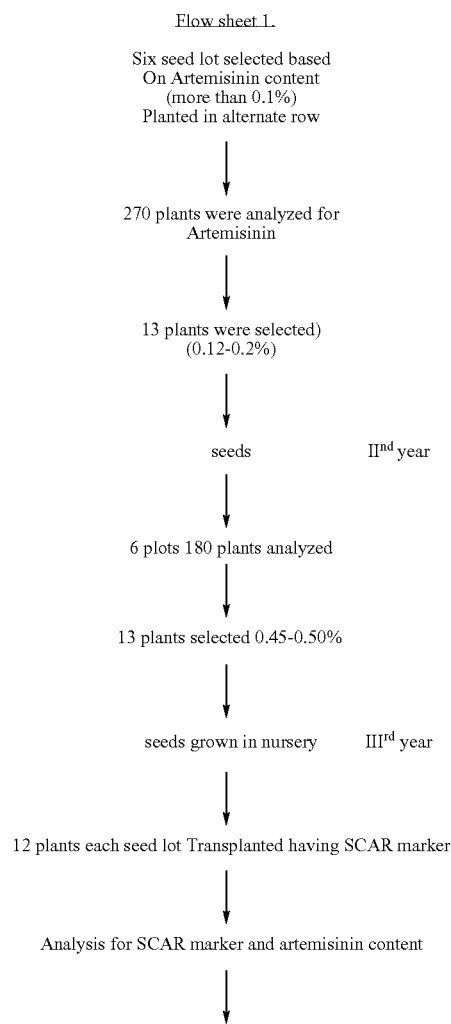

Flow sheet 1.

Six seed lot selected based On Artemisinin content (more than 0.1%) Planted in alternate row 270 plants were analyzed for Artemisinin 13 plants were selected) (0.12-0.2%)

seeds    II$^{nd}$ year 6 plots 180 plants analyzed 13 plants selected 0.45-0.50% seeds grown in nursery    III$^{rd}$ year 12 plants each seed lot Transplanted having SCAR marker Analysis for SCAR marker and artemisinin content

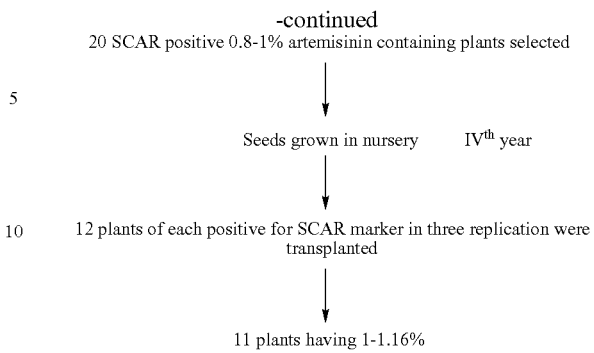

-continued

20 SCAR positive 0.8-1% artemisinin containing plants selected

Seeds grown in nursery    IV$^{th}$ year 12 plants of each positive for SCAR marker in three replication were transplanted 11 plants having 1-1.16%

Genetic Advancement

The key metabolite synthesis (Artemisinin content) was studied for genetic advancement which showed an upward trend beginning with 17.33% increase in the mean artemisinin content for the first year, crossing 50% in second year, 60% in third year and remaining at 42.06% in fourth year. The advancement in artemisinin content was calculated as per Singh and Chaudhary (1977) (Singh R K and Chaudhary B D (1977). Biometrical methods in quantitative genetic analysis. Kalyani Publications, New Delhi.

The seeds obtained from these selected plants four single plant seed lots (CIMAP-G1, CIMAP-G2, CIMAP-G3, CIMAP-G4) were evaluated in the field at CIMAP Farm, Lucknow, Utterpradesh, Lucknow, India.

Experimental (Agronomic) Details *Artemisia annua* evaluation trials at CIMAP research farm.

| Component (s) | 2001-02 | 2002-03 |
|---|---|---|
| Design | RBD | RBD |
| Genotypes (with check) | Five | Five |
| Manuring (FYM) | 10 t/ha | 10 t/ha |
| Fertilization (NPK) | 80:40:40 | 80:40:40 |
| Row to row distance | 50 cm | 50 cm |
| Plant to plant distance | 30 cm | 30 cm |
| Plot size | 12.5 sq m (Net) | 15.75 sq m (Net) |
| DOT | 23/02/02 | 10/03/03 |
| DOH (I) | 03/06/02 (100 DAP) | 02/06/03 (84 DAP) |
| DOH (II) | 29/07/02 (156 DAP) | 31/07/03 (143 DAP) |
| DOH (III) | 13/09/02 (202 DAP) | 11/09/03 (185 DAP) |
| DOH (Seed) | 16/12/02 | 28/11/03 |

*50 kg/ha N was applied after every cut (harvest)
DOT: Date of transplantation
DOH: Date of harvesting Four selected genotypes from these lots were selected among each other and with the best check 'Jeevan Raksha'. Herb yield data with regard to advanced lines of *Artemisia annua* along with the check during the evaluation trials at CIMAP research farm, Lucknow has been provided below. The genotype CIMAP-G2 (CIM-Arogya) yielded maximum dry leaves compared to other genotypes in the trial.

| | Fresh herb (q/ha) | | Dry leaves (q/ha) | |
|---|---|---|---|---|
| Genotype | 2001-02 | 2002-03 | 2001-02 | 2002-03 |
| CIMAP-G1 | 523.6 | 466.67 | 55.56 | 48.09 |
| CIMAP-G2 | 553.0 | 478.45 | 58.40 | 48.89 |
| CIMAP-G3 | 559.8 | 444.45 | 56.04 | 45.71 |

-continued

| | Fresh herb (q/ha) | | Dry leaves (q/ha) | |
| --- | --- | --- | --- | --- |
| Genotype | 2001-02 | 2002-03 | 2001-02 | 2002-03 |
| CIMAP-G4 | 422.0 | 439.69 | 42.00 | 46.27 |
| Jeevan Raksha | 438.4 | 426.19 | 43.60 | 42.30 |
| F-value | 7.55** | 6.2** | 10.79** | 6.31** |
| gm | 499.36 | 451.11 | 51.12 | 46.25 |
| sem | 23.6 | 8.5 | 2.34 | 10.02 |
| cv | 9.45 | 3.77 | 9.16 | 4.41 |
| cd (1%) | 101.88 | 36.71 | 10.11 | 4.4 |
| cd (5%) | 72.7 | 26.19 | 7.21 | 3.14 |

The plant genotype of *Artemisia annua* of the invention was named as 'CIM-Arogya' and referred in the same name in the patent document. The genotype can be grown as a uniform population of high artemisinin yielding plants with rouging at nursery Taxonomic Description of 'CIM-Arogya'

The plant is usually single stemmed reaching about 2 m in height with alternate branches and alternate deeply dissected aromatic leaves ranging from 2.5 to 5.0 cm in length. Tiny greenish yellow nodding flowers (capitula) only 2 or numerous imbricate bracts enclose 3 mm in diameter. Capitula is displayed in loose panicle containing numerous central bisexual florets and marginal pistillate florets, the latter extruding stigmas prior to the central flower. The receptacles is glabrous, not chaffy and triangular in shape. Both florets and receptacle bear abundant 10-celled biseriate glandular trichomes, which are the source of artemisinin and highly aromatic volatile oils (essential oil).

The colour codes are in accordance with the "RHS colour chart published by The Royal Horticultural Society, 80 Vincent Square, London SW1P 2PE, 1995.

The genotype 'CIM-Arogya' possessing the traits of increased herb yield than the other check varieties and genotypes. The genotype is having higher biomass leading to high artemisinin yield. Its genetic make up is distinct in terms of DNA profile. The genotype in the population has expressed a genetic enhancement of artemisinin content to a very high content of artemisinin through strategic marker aided selection indicating the distinctiveness from the parent genotype. The plant has a unique globular canopy.

Randomly Amplified Polymorphic DNA analysis: The RAPD analysis of the genotype 'CIM-Arogya' were unambiguously able to establish its distinct identity as completely different from the check genotypes. The 20 MAP primers (MAP 01 to MAP 20) synthesized in the laboratory using ABI 392 DNA synthesizer, with the sequence AAATCG-GAGC, GTCCTACTCG, GTCCTTAGCG, TGCGC-GATCG, AACGTACGCG, GCACGCCGGA, CACCCT-GCGC, CTATCGCCGC, CGGGATCCGC, GCGAATTCCG, CCCTGCAGGC, CCAAGCTTGC, GTGCAATGAG, AGGATACGTG, AAGATAGCGG, GGATCTGAAC, TTGTCTCAGG, CATCCCGAAC, GGACTCCACG, AGCCTGACGC were used for the analysis to differentiate among the genotypes.

From RAPD analysis the profiles were studied and similarity indices were calculated which were put into a matrix. This matrix was used to produce a graphic phenogram by means of UPGMA (unweighted pair group method with arithmetic average) cluster analysis. As represented in the phenogram provided below (FIG. 1) the clone of the invention is quite different from the other varieties.

The invention claimed is:

1. A new and distinct genotype of *Artemisia annua* 'CIM-Arogya', developed through marker assisted breeding, possessing the following combination of characters:
Genus *Artemisia*
Species *annua*
Family Asteraecae
Common name Qinghao
Plant height 280-305 cm
Plant canopy Oval
Growth habit Erect
Branching sympodial branching pattern
Stem: ingle, round hard woody green (137D)
  Stem width 5-12 cm (app)
Number of Branches:—
primary branches:—55-65—
Secondary branches per primary branch:—50-60—
Tertiary branches per secondary branch:—37-45
Range of length of Internodes
Main stem—4-6 cm at bottom; 10-12 cm at middle, 2-5 cm at the top
Primary branch 2-5 cm at bottom, 8-11 cm at middle, 2-4 cm at the top
Secondary branch 8-11 cm at the bottom, 5-7 cm at the middle, 1-3 cm at the top
Tertiary branch 3-5 cm at the bottom, 1-3 cm at the middle, 0.5-1.5 cm at the top
Leaf—Green (137 B)
Texture—Thin and flexible
Surface—Smooth non pubescent
Shape—Pinnately compound leaf
Margin—Pinnetisected
Tip—Acute
Petiol length—2.5-3.50 cm
Lamina length—5-7 cm
Lamina width—4-5 cm
Inflorescence—Capitulum (head)
Flower—Arranged in whorls. Colour yellow group (7A)
Two types of flowers Disc florets and Ray florets.
Disc florets are bisexual and ray florets are unisexual (female)
Colour Greenish yellow 2-3 mm in diameter
Receptacles Glabrous
Calyx Bracteates
Corolla Sympelatous, tubular top split in to 5 lobes in Disc florets and 2-3
lobes in Ray florets (legulate)
Androecium 5 stamens, Anther lobes are fused and filaments are free
Colour Yellowish
Gynoecium Unilocular, inferior bifid stigma.
Colour yellowish
Time of flowering—198 days.
Seed setting 240 days (app)
Artemisinin content 0.9 to 1.1%
Artemesinic acid 0.002-0.004%
Oil content 0.35-0.45%
alternate deeply dissected aromatic leaves ranging between 2.5 to 5.0 cm in length.
tiny yellow nodding flowers (capitula)

capitula in loose panicle containing numerous central bisexual florets and marginal pistillate florets
receptacle is glabrous
florets and receptacle bear abundant 10-celled biseriate trichomes
globular canopy
dry leaf yield of about 50 Q per hectare
flowers (7A) arranged in a head or Capitulum.

* * * * *

SEQUENCE LISTING

```
<160> NUMBER OF SEQ ID NOS: 23

<210> SEQ ID NO 1
<211> LENGTH: 10
<212> TYPE: DNA
<213> ORGANISM: ARTIFICIAL
<220> FEATURE:
<223> OTHER INFORMATION: MAP Primer

<400> SEQUENCE: 1
aaatcggagc                                                          10

<210> SEQ ID NO 2
<211> LENGTH: 10
<212> TYPE: DNA
<213> ORGANISM: ARTIFICIAL
<220> FEATURE:
<223> OTHER INFORMATION: MAP Primer

<400> SEQUENCE: 2
gtcctactcg                                                          10

<210> SEQ ID NO 3
<211> LENGTH: 10
<212> TYPE: DNA
<213> ORGANISM: ARTIFICIAL
<220> FEATURE:
<223> OTHER INFORMATION: MAP Primer
```

```
<400> SEQUENCE: 3
gtccttagcg                                                          10

<210> SEQ ID NO 4
<211> LENGTH: 10
<212> TYPE: DNA
<213> ORGANISM: ARTIFICIAL
<220> FEATURE:
<223> OTHER INFORMATION: MAP Primer

<400> SEQUENCE: 4
tgcgcgatcg                                                          10

<210> SEQ ID NO 5
<211> LENGTH: 10
<212> TYPE: DNA
<213> ORGANISM: ARTIFICIAL
<220> FEATURE:
<223> OTHER INFORMATION: MAP Primer

<400> SEQUENCE: 5
aacgtacgcg                                                          10

<210> SEQ ID NO 6
<211> LENGTH: 10
<212> TYPE: DNA
<213> ORGANISM: ARTIFICIAL
<220> FEATURE:
<223> OTHER INFORMATION: MAP Primer

<400> SEQUENCE: 6
gcacgccgga                                                          10

<210> SEQ ID NO 7
<211> LENGTH: 10
<212> TYPE: DNA
<213> ORGANISM: ARTIFICIAL
<220> FEATURE:
<223> OTHER INFORMATION: MAP Primer

<400> SEQUENCE: 7
caccctgcgc                                                          10

<210> SEQ ID NO 8
<211> LENGTH: 10
<212> TYPE: DNA
<213> ORGANISM: ARTIFICIAL
<220> FEATURE:
<223> OTHER INFORMATION: MAP Primer

<400> SEQUENCE: 8
ctatcgccgc                                                          10

<210> SEQ ID NO 9
<211> LENGTH: 10
<212> TYPE: DNA
<213> ORGANISM: ARTIFICIAL
<220> FEATURE:
<223> OTHER INFORMATION: MAP Primer

<400> SEQUENCE: 9
cgggatccgc                                                          10

<210> SEQ ID NO 10
```

```
<211> LENGTH: 10
<212> TYPE: DNA
<213> ORGANISM: ARTIFICIAL
<220> FEATURE:
<223> OTHER INFORMATION: MAP Primer

<400> SEQUENCE: 10
gcgaattccg                                                              10

<210> SEQ ID NO 11
<211> LENGTH: 10
<212> TYPE: DNA
<213> ORGANISM: ARTIFICIAL
<220> FEATURE:
<223> OTHER INFORMATION: MAP Primer

<400> SEQUENCE: 11
ccctgcaggc                                                              10

<210> SEQ ID NO 12
<211> LENGTH: 10
<212> TYPE: DNA
<213> ORGANISM: ARTIFICIAL
<220> FEATURE:
<223> OTHER INFORMATION: MAP Primer

<400> SEQUENCE: 12
ccaagcttgc                                                              10

<210> SEQ ID NO 13
<211> LENGTH: 10
<212> TYPE: DNA
<213> ORGANISM: ARTIFICIAL
<220> FEATURE:
<223> OTHER INFORMATION: MAP Primer

<400> SEQUENCE: 13
gtgcaatgag                                                              10

<210> SEQ ID NO 14
<211> LENGTH: 10
<212> TYPE: DNA
<213> ORGANISM: ARTIFICIAL
<220> FEATURE:
<223> OTHER INFORMATION: MAP Primer

<400> SEQUENCE: 14
aggatacgtg                                                              10

<210> SEQ ID NO 15
<211> LENGTH: 10
<212> TYPE: DNA
<213> ORGANISM: ARTIFICIAL
<220> FEATURE:
<223> OTHER INFORMATION: MAP Primer

<400> SEQUENCE: 15
aagatagcgg                                                              10

<210> SEQ ID NO 16
<211> LENGTH: 10
<212> TYPE: DNA
<213> ORGANISM: ARTIFICIAL
<220> FEATURE:
<223> OTHER INFORMATION: MAP Primer

<400> SEQUENCE: 16
```
ggatctgaac                                                              10

<210> SEQ ID NO 17
<211> LENGTH: 10
<212> TYPE: DNA
<213> ORGANISM: ARTIFICIAL
<220> FEATURE:
<223> OTHER INFORMATION: MAP Primer

<400> SEQUENCE: 17
ttgtctcagg                                                              10

<210> SEQ ID NO 18
<211> LENGTH: 10
<212> TYPE: DNA
<213> ORGANISM: ARTIFICIAL
<220> FEATURE:
<223> OTHER INFORMATION: MAP Primer

<400> SEQUENCE: 18
catcccgaac                                                              10

<210> SEQ ID NO 19
<211> LENGTH: 10
<212> TYPE: DNA
<213> ORGANISM: ARTIFICIAL
<220> FEATURE:
<223> OTHER INFORMATION: MAP Primer

<400> SEQUENCE: 19
ggactccacg                                                              10

<210> SEQ ID NO 20
<211> LENGTH: 10
<212> TYPE: DNA
<213> ORGANISM: ARTIFICIAL
<220> FEATURE:
<223> OTHER INFORMATION: MAP Primer

<400> SEQUENCE: 20
agcctgacgc                                                              10

<210> SEQ ID NO 21
<211> LENGTH: 932
<212> TYPE: DNA
<213> ORGANISM: ARTIFICIAL
<220> FEATURE:
<223> OTHER INFORMATION: MAP Primer

<400> SEQUENCE: 21
aagcttgctg aacgcatcgg tgttactgcc gcagcccgtg aactcagcct gtatgaatca        60
caactctaca actggcgcag taaacagcaa aatcagcaga cgtcttctga acgtgaactg       120
gagatgtcta ccgagattgc acgtctcaaa cgccagctgg cagaacggga tgaagagctg       180
gctatcctcc aaaaggccgc gacatacttc gcgaagcgcc tgaaatgaag tatgtcttta       240
ttgaaaaaca tcaggctgag ttcagcatca aagcaatgtg ccgcgtgctc cgggtggccc       300
gcagcggctg gtatacgtgg gtgtcagcgg cggacaagga taagcccgcg taagcagttc       360
cgccaacact gcacaggggg ttgtctcgcg ggttttaccc cgggtcaaac aagcgttacc       420
ggtgccccac gcttgaccgg atgacctgcg gtgctcaggg ttacccttta acgtaaaaaa       480
cccgtggcgc aagcttgccc cggtcaggga ctgaaggcaa aggcctcccg gaagttcagc       540

```
ccggtcagct accgcggcac acgggcctgc ctgtgtcaga aaatctgttg gagcaggatt     600
tttacgccca gtggcccgaa ccagaagtgg gcaggagaca tcacgtactt acgtacagat    660
gaaggctggc tgtatctggc agtggtcatt gacctgtggt cacgtgccgt tattggctgg    720
tcaatgtcgc cacgcatgac ggcgcaactg gcctgcgatg ccctgcagat ggcgctgtgg    780
cggcgtaaga ggccccggaa cgttatcgtt cacacggacc gtggaggcca gtactgttca    840
gcagattatc aggcgcaact gaagcggcat aatctgcgtg gaagtatgag cgcaaaaggt    900
tgctgctacg ataatgcctg cgtggaaagc tt                                  932

<210> SEQ ID NO 22
<211> LENGTH: 22
<212> TYPE: DNA
<213> ORGANISM: ARTIFICIAL
<220> FEATURE:
<223> OTHER INFORMATION: MAP Primer

<400> SEQUENCE: 22
ccaagcttgc tgaacgcatc gg                                              22

<210> SEQ ID NO 23
<211> LENGTH: 26
<212> TYPE: DNA
<213> ORGANISM: ARTIFICIAL
<220> FEATURE:
<223> OTHER INFORMATION: MAP Primer

<400> SEQUENCE: 23
ccaagcttgc cacgcagggc attatc                                          26
```